(12) United States Patent
Ino et al.

(10) Patent No.: US 6,638,923 B2
(45) Date of Patent: Oct. 28, 2003

(54) ESTRA-1,3,5(10),16-TETRAENE DERIVATIVES

(75) Inventors: Yoji Ino, Shizuoka (JP); Nobuyoshi Amishiro, Shizuoka (JP); Taisuke Nakata, Shizuoka (JP); Hiroyuki Ishida, Shizuoka (JP); Shiro Akinaga, Shizuoka (JP); Chikara Murakata, Shizuoka (JP); Pui-Kai Li, Galloway, OH (US)

(73) Assignees: Kyowa Hakko Kogyo Co., Ltd., Tokyo (JP); Duquesne University of the Holy Ghost, PA (US)

( * ) Notice: Subject to any disclaimer, the term of this patent is extended or adjusted under 35 U.S.C. 154(b) by 0 days.

(21) Appl. No.: 09/859,599

(22) Filed: May 18, 2001

(65) Prior Publication Data

US 2002/0058651 A1 May 16, 2002

Related U.S. Application Data

(62) Division of application No. 09/548,930, filed on Apr. 13, 2000, now Pat. No. 6,262,043.
(60) Provisional application No. 60/129,037, filed on Apr. 13, 1999.

(51) Int. Cl.$^7$ .............................. A61K 31/56; C07J 3/00
(52) U.S. Cl. ........................................ 514/182; 552/611
(58) Field of Search ........................... 552/611; 514/182

(56) References Cited

U.S. PATENT DOCUMENTS

| | | | |
|---|---|---|---|
| 4,910,226 A | 3/1990 | Holt et al. | 514/573 |
| 4,946,834 A | 8/1990 | Holt et al. | 514/119 |
| 5,556,847 A | 9/1996 | Johnson et al. | 514/178 |
| 5,567,831 A | 10/1996 | Li | 554/43 |
| 5,571,933 A | 11/1996 | Li et al. | 552/521 |
| 5,604,215 A | 2/1997 | Reed et al. | 514/178 |
| 5,616,574 A | 4/1997 | Reed et al. | 514/178 |
| 5,763,432 A | 6/1998 | Tanabe et al. | 514/176 |
| 5,763,492 A | 6/1998 | Johnson et al. | 514/603 |
| 5,866,603 A | 2/1999 | Li et al. | 514/303 |
| 5,880,115 A * | 3/1999 | Li et al. | 514/178 |
| 6,288,050 B1 * | 9/2001 | Li et al. | 514/182 |

FOREIGN PATENT DOCUMENTS

| | | |
|---|---|---|
| WO | WO 93/14107 | 7/1993 |
| WO | WO 95/21185 | 8/1995 |
| WO | WO 97/30041 | 8/1997 |
| WO | WO 97/32872 | 9/1997 |
| WO | WO 97/40062 | 10/1997 |
| WO | WO 98/11124 | 3/1998 |
| WO | WO 98/24802 | 6/1998 |
| WO | WO 98/42729 | 10/1998 |
| WO | WO 99/03876 | 1/1999 |

OTHER PUBLICATIONS

Li et al., "Development of potent non–estrogenic estrone sulfatase inhibitors." Steroids, vol. 63, pp. 425–432, 1998.*
International Journal of Cancer, vol. 63 (1995), pp. 106–111.
Cancer Research, vol. 56 (Nov. 1996), pp. 4950–4955.
Cancer Research, vol. 53 (Jan. 1993), pp. 298–303.
Bioorganic & Medicinal Chemistry Letters, vol. 3 (1993), pp. 313–318.
Journal of Medicinal Chemistry, vol. 37 (1994), pp. 219–221.
Steroids, vol. 58 (Mar. 1993), pp. 106–111.
Journal of Steroid Biochemistry and Molecular Biology, vol. 50 (1994), pp. 261–266.
Steroids, vol. 60 (1995), pp. 299–306.
Journal of Steroid Biochemistry and Molecular Biology, vol. 59 (1996), pp. 83–91.
Journal of Steroid Biochemistry and Molecular Biology, vol. 48 (1994), pp. 563–566.
Journal of Steroid Biochemistry and Molecular Biology, vol. 45 (1993), pp. 383–390.
Biochemistry, vol. 36 (1997), pp. 2586–2594.
Journal of Steroid Biochemistry and Molecular Biology, vol. 64 (1998), pp. 269–275.
Bioorganic & Medicinal Chemistry Letters, vol. 8 (1998), pp. 1891–1896.
Canadian Journal of Physiology and Pharmacology, vol. 76 (1998), pp. 99–109.
Cancer Research vol. 57 (1997), pp. 702–707.
Journal of Steroid Biochemistry and Molecular Biology, vol. 68 (1997), pp. 31–40.
Journal of Steroid Biochemistry and Molecular Biology, vol. 63 (1997), pp. 9–15.
Biorganic & Medicinal Chemistry Letters, vol. 9 (1999), pp. 141–144.
Steroids, vol. 63 (1998), pp. 425–432.
Journal of Medicinal Chemistry, vol. 33 (1990), pp. 937–942.
Journal of Medicinal Chemistry, vol. 33 (1990), pp. 943–950.

* cited by examiner

*Primary Examiner*—Barbara P. Badio
(74) *Attorney, Agent, or Firm*—Fitzpatrick, Cella, Harper & Scinto

(57) ABSTRACT

Estra-1,3,5(10),16-tetraene derivatives represented by the following formula (I):

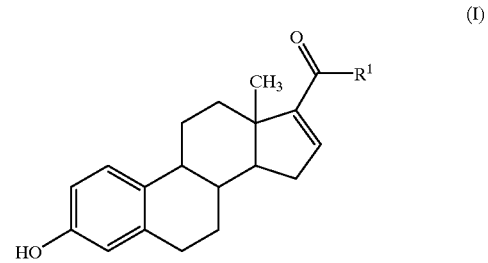

(I)

(wherein $R^1$ is as defined by the present specification.

16 Claims, No Drawings

ESTRA-1,3,5(10),16-TETRAENE DERIVATIVES

This application is a division of application Ser. No. 09/548,930, filed on Apr. 13, 2000, now U.S. Pat. No. 6,262,043 which claims benefit to U.S. provisional application No. 60/129,037 filed Apr. 13, 1999.

BACKGROUND OF THE INVENTION

1. Field of the Invention

The present invention relates to estra-1,3,5 (10),16-tetraene derivatives or pharmaceutically acceptable salts thereof, which show inhibitory activity against steroid sulfatase and are useful in treating or preventing hormone dependent diseases.

2. Brief Description of the Background Art

In post-menopausal women, estrogen levels in breast tumors are is at least ten times higher than those in plasma, and such high estrogen levels in breast tumors are caused by the function of steroid sulfatase (estrone sulfatase) which hydrolyzes estrone sulfate into estrone. Consequently, steroid sulfatase inhibitors are effective therapeutic agents in treating estrone dependent breast cancers and are also considered to be effective in preventing or treating other diseases concerned by estrones, such as endometrial cancers, ovarian cancers, prostate cancers, and adenomyosis of uterus.

Estrone-3-sulfamate (EMATE) has been reported as a typical inhibitor of steroid sulfatase (*International Journal of Cancer*, 63: 106 (1995); U.S. Pat. No. 5,616,574). However, it has been revealed recently that EMATE shows an estrogenic activity, and it is shown that EMOTE is not useful for the treatment of estrone dependent diseases (*Cancer Research*, 56: 4950 (1996)).

Examples of other known steroid type of steroid sulfatase inhibitors include estrone-3-methylthiophosphonate, estrone-3-methylphosphonate, estrone-3-phenylphosphonothioate, and estrone-3-phenylphosphonate (*Cancer Research*, 53: 298 (1993); *Bioorganic & Medicinal Chemistry Letters*, 3: 313 (1993); U.S. Pat. No. 5,604,215), estrone-3-sulfamate derivatives (*Journal of Medicinal Chemistry*, 37: 219 (1994)), 3-desoxyestrone-3-sulfonate derivatives (*Steroids*, 58: 106 (1993); *The Journal of Steroid Biochemistry and Molecular Biology*, 50: 261 (1994)), 3-desoxyestrone-3-methylsulfonate derivatives (*Steroids*, 60: 299 (1995)), estrone-3-amino derivatives (*The Journal of Steroid Biochemistry and Molecular Biology*, 59: 83 (1996); U.S. Pat. No. 5,571,933; U.S. Pat. No. 5,866,603), vitamin D₃ derivatives (*The Journal of Steroid Biochemistry and Molecular Biology*, 48: 563 (1994)), dehydroepiandrosterone derivatives (*The Journal of Steroid Biochemistry and Molecular Biology*, 45: 383 (1993); Biochemistry, 36: 2586 (1997)), A-ring modified derivatives of estrone-3-sulfamate (*The Journal of Steroid Biochemistry and Molecular Biology*, 64: 269 (1998); WO 98/24802; WO 98/32763), 17-alkylestradiol derivatives (*Bioorganic & Medicinal Chemistry Letters*, 8: 1891 (1998)), 3-substituted-D-homo-1,3,5(10)-estratriene derivatives (WO 98/11124), D-ring modified derivatives of estrone (WO 98/42729), and B-, C- and D-ring modified derivatives of estrone (*Canadian Journal of Physiology and Pharmacology*, 76: 99 (1998)).

Examples of known non-steroid type of steroid sulfatase inhibitors include tetrahydronaphthol derivatives (*Journal of Medicinal Chemistry*, 37: 219 (1994)), 4-methylcoumarin-7-sulfamate (*Cancer Research*, 56: 4950 (1996); WO 97/30041), tyramine derivatives and phenol derivatives (*Cancer Research*, 57: 702 (1997); Biochemistry, 36: 2586 (1997); *The Journal of Steroid Biochemistry and Molecular Biology*, 68: 31 (1999); U.S. Pat. No. 5,567,831), flavonoids (*The Journal of Steroid Biochemistry and Molecular Biology*, 63: 9 (1997); WO 97/32872), and 4-hydroxytamoxifen derivatives (*The Journal of Steroid Biochemistry and Molecular Biology*, 45: 383 (1993); *Bioorganic & Medicinal Chemistry Letters*, 9: 141 (1999)).

It is also reported that steroid sulfamates and tyramine derivatives have the effect of memory enhancement (U.S. Pat. No. 5,556,847; U.S. Pat. No. 5,763,492).

Also, it has been reported recently that certain 17-amide derivatives, such as 17β-(N-alkylcarbamoyl)estra-1,3,5(10)-triene-3-sulfamates and 17β-(N-alkanoyl)estra-1,3,5(10)-triene-3-sulfamates (*Steroids*, 63: 425 (1998); WO 99/03876), show inhibitory activity against steroid sulfatase.

The following 17-amide derivatives (Compound A) described in WO 99/03876 are synthetic intermediates of compounds in which the phenolic hydroxyl group at the 3-position is substituted with sulfamoyloxy, and the substituent on the amide group is limited to straight chain alkyl having 4 or more carbon atoms. It is not known that Compound A shows inhibitory activity against steroid sulfatase.

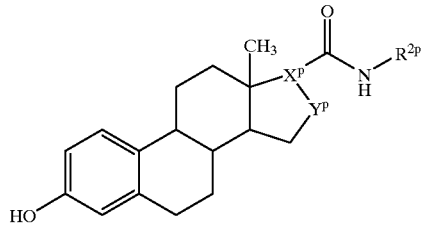

(A)

(In the above formula, $R^{2p}$ represents straight-chain alkyl having 4 to 14 carbon atoms; $X^p$ represents methine, or forms a double bond together with $Y^p$; and $Y^p$ represents methylene, or forms a double bond together with $X^p$.)

Additionally, as examples of Pd-catalyzed carbonylation and as synthetic intermediates of steroid 5α-reductase, 17-amide derivatives and 17-carboxylic acid derivatives (Compound B) shown below in which a hydroxyl group at the 3-position is substituted with methoxy, trifluoromethanesulfonyloxy, acetoxy, methanesulfonyloxy, or benzoxy, have been reported (for example, *Tetrahedron Letters*, 26: 1109 (1985); *Tetrahedron Letters*, 33: 3939 (1992); *Journal of Medicinal Chemistry*, 33: 937 (1990); *Journal of Medicinal Chemistry*, 33: 943 (1990); Synthesis, 831 (1995); *Helvetica Chimica Acta*, 81: 2264 (1998); U.S. Pat. Nos. 4,946,834 and 4,910,226). Compound C in which a double bond is reduced is also known (for example, *The Journal of Organic Chemistry*, 59: 6683 (1994); WO 93/14107; WO 95/21185; WO 97/40062). However, it has not been reported that any of these compounds shows inhibitory activity against steroid sulfatase.

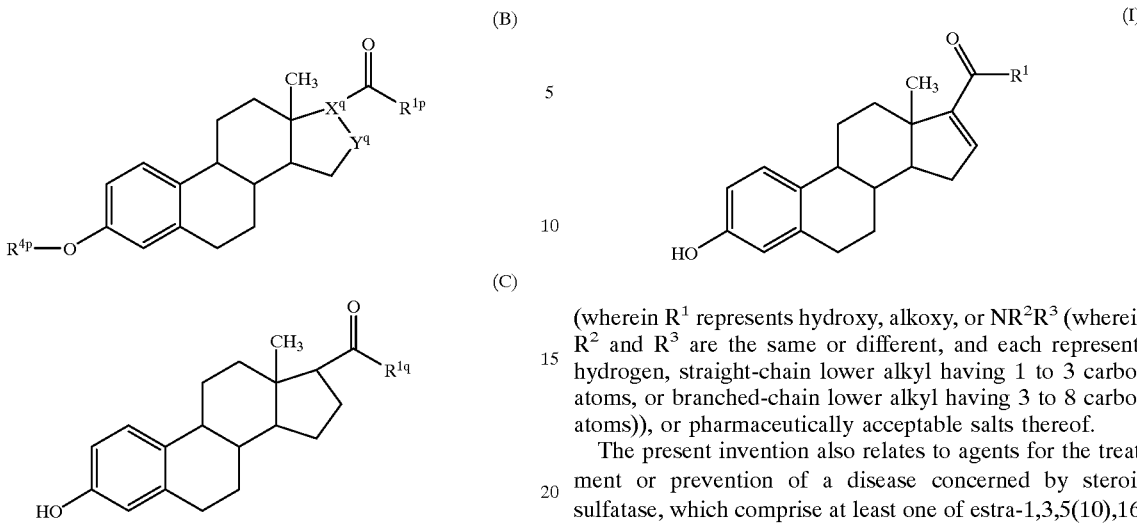

(In the above formulae, when $X^q$ and $Y^q$ are combined to represent a double bond, $R^{1p}$ represents hydroxy, isopropoxy, methoxy, 2-iodo-4-methylphenoxy, or $NR^{2q}R^{3q}$ (wherein $R^{2q}$ and $R^{3q}$ are the same or different, and each represents hydrogen, ethyl, isopropyl, or tert-butyl, or $R^{2q}$ and $R^{3q}$ are combined together with the adjacent nitrogen atom to represent pyrrolidinyl, morpholino, or piperidino), and $R^{4p}$ represents methyl, trifluoromethanesulfonyl, acetyl, methanesulfonyl, or benzoyl. When $X^q$ is methine and $Y^q$ is methylene, $R^{1p}$ represents methoxy or $NR^{2r}R^{3r}$ (wherein $R^{2r}$ and $R^{3r}$ are the same or different, and each represents hydrogen, isopropyl, or substituted alkyl), and $R^{4p}$ represents methyl, trifluoromethanesulfonyl, or methanesulfonyl. $R^{1q}$ represents hydroxy or $NR^{2s}R^{3s}$ (wherein $R^{2s}$ and $R^{3s}$ are the same or different, and each represents hydrogen, isopropyl, tert-butyl, or substituted alkyl).)

Steroid sulfatase inhibitors, which do not show estrogenic activity, and are more metabolically stable and more selective for the enzyme, are desired.

SUMMARY OF THE INVENTION

An object of the present invention is to provide estra-1,3,5(10),16-tetraene derivatives or pharmaceutically acceptable salts thereof, which show inhibitory activity against steroid sulfatase and are useful in treating or preventing hormone dependent diseases.

The present invention relates to estra-1,3,5(10),16-tetraene derivatives represented by the following formula (I):

(wherein $R^1$ represents hydroxy, alkoxy, or $NR^2R^3$ (wherein $R^2$ and $R^3$ are the same or different, and each represents hydrogen, straight-chain lower alkyl having 1 to 3 carbon atoms, or branched-chain lower alkyl having 3 to 8 carbon atoms)), or pharmaceutically acceptable salts thereof.

The present invention also relates to agents for the treatment or prevention of a disease concerned by steroid sulfatase, which comprise at least one of estra-1,3,5(10),16-tetraene derivatives represented by formula (I) or pharmaceutically acceptable salts thereof Furthermore, the present invention relates to a method for treating or preventing a disease concerned by steroid sulfatase, which comprises administering at least one of the estra-1,3,5(10),16-tetraene derivatives represented by formula (I) or pharmaceutically acceptable salts thereof.

DETAILED DESCRIPTION OF THE INVENTION

This application is based on U.S. provisional application No. 60/129,037 filed on Apr. 13, 1999, the entire contents of which are incorporated hereinto by reference.

Hereinafter, the compound represented by formula (I) is referred to as Compound (I). Compounds of other formula numbers are also called similarly. In the definition of respective groups of Compound (I), the term "lower" means that the number of carbon atoms is from 1 to 8, unless otherwise indicated.

Examples of the straight-chain lower alkyl having 1 to 3 carbon atoms include methyl, ethyl, and propyl; and examples of the branched-chain lower alkyl having 3 to 8 carbon atoms include isopropyl, isobutyl, sec-butyl, tert-butyl, isopentyl, neopentyl, isooctyl and the like. Examples of the alkyl moiety of alkoxy include straight- or branched-chain groups having 1 to 14 carbon atoms, such as methyl, ethyl, propyl, isopropyl, butyl, isobutyl, sec-butyl, tert-butyl, pentyl, isopentyl, neopentyl, hexyl, heptyl, octyl, isooctyl, decyl, dodecyl, tetradecyl and the like.

Among Compound (I), compounds in which $R^1$ is hydroxy or $NR^2R^3$ (wherein $R^2$ and $R^3$ have the same meanings as defined above) are preferred, and compounds in which $R^1$ is hydroxy are most preferred.

Examples of the pharmaceutically acceptable salt of Compound (I) include metal salts, ammonium salts, organic amine addition salts, amino acid addition salts and the like. Alkali metal salts, such as lithium salt, sodium salt, potassium salt and the like, and alkaline earth metal salts, such as magnesium salt, calcium salt and the like, as well as aluminum salt, zinc salt and the like, can be exemplified as the metal salts; ammonium, tetramethylammonium and the like can be exemplified as the ammonium salts, addition salts with morpholine, piperidine and the like can be exemplified as the organic amine addition salts; and addition salts with glycine, phenylalanine, lysine and the like can be exemplified as the amino acid addition salts.

Compound (I) of the present invention is generally prepared using estrone or various estra-1,3,5(10)-triene derivatives as the starting compound, and certain members of Compound (I) may exist in various isomer forms, such as stereoisomers, position isomers, tautomers and the like. All of these possible isomers and their mixtures are included in the scope of the present invention, and such mixtures may have any optional mixture ratio.

Next, production methods of Compound (I) are described.

Production Method 1

Compound (Ia) can be obtained by hydrolyzing a nitrile group of Compound (D) or Compound (E) in which the 3-position is protected, which can be prepared from estrone according to known methods (for example, see *Helvetica Chimica Acta*, 81: 2264 (1998); *The Journal of Organic Chemistry*, 59: 6683 (1994); *Journal of the Chemical Society Chemical Communications*, p. 756 (1989); and *The Biochemical Journal*, 93: 512 (1964)).

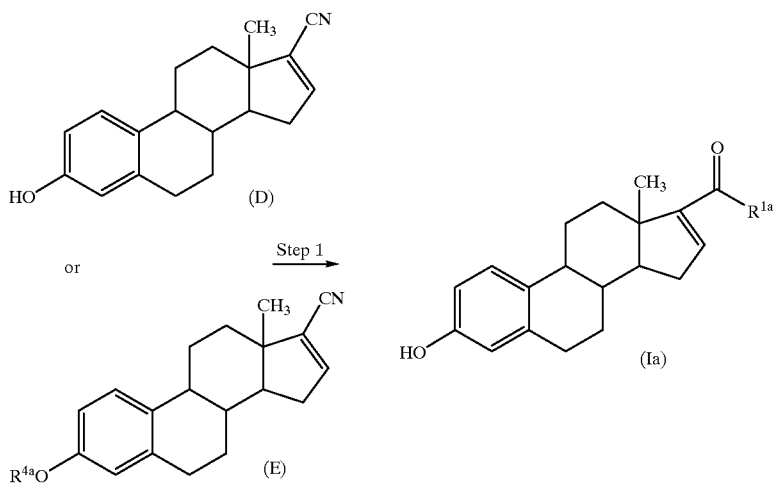

(In the above formula, $R^{1a}$ is hydroxy or amino; and $R^{4a}$ is acetyl, benzoyl, methanesulfonyl, or p-toluenesulfonyl.)

Step 1

Compound (Ia) can be obtained by allowing Compound (D) or Compound (E) to react with an acid or a base.

Examples of the solvent include tetrahydrofuran (THF), 1,4-dioxane, 1,2-dimethoxyethane, methanol, ethanol, tert-butanol, 1-hexanol, ethylene glycol, 2-methoxyethanol, dimethylformamide (DMF), dimethyl sulfoxide (DMSO), 1,3-dimethyl-2-imidazolidinone (DMI), water, toluene, dichloromethane, chloroform, 1,2-dichloroethane and the like, which may be used alone or as a mixture thereof.

The production process of Compound (I) mainly comprises a hydrolysis step of nitrile (Production Method 1), a deprotection step at the 3-position (Production Method 2), a hydrolysis step of ester/amide (Production Method 3), and an amidation/esterification step (Production Method 4), and the desired compound can be prepared by combining these reaction steps depending on each purpose.

When each group defined in the following production methods changes under reaction conditions or is not appropriate in carrying out the method, the desired compound can be obtained by using an introduction-elimination method of protecting groups, usually used in the synthetic organic chemistry, (for example, see *Protective Groups in Organic Synthesis*, edited by T. W. Greene, John Wiley & Sons Inc. (1981)) or the like. The order of reaction steps, such as introduction of substituents, may be changed, if necessary. Additionally, protecting groups of the 3-position phenolic hydroxyl group of steroids to be used in the process for obtaining the desired compound are not limited to those which are described in the following production methods, and protecting groups usually used in the synthetic organic chemistry (for example, methoxymethyl, methoxyethyl, allyl, tetrahydropyranyl, phenacyl, p-methoxybenzyl, tert-butyldimethylsilyl, pivaloyl, methoxycarbonyl, vinyloxycarbonyl and the like) can be used and their elimination can also be carried out by any elimination method usually used in the synthetic organic chemistry (for example, see *Protective Groups in Organic Synthesis*, edited by T. W. Greene, John Wiley & Sons Inc. (1981)).

Examples of the acid include hydrochloric acid, hydrobromic acid, nitric acid, phosphoric acid, polyphosphoric acid, methanesulfonic acid, p-toluenesulfonic acid, formic acid, acetic acid, trifluoroacetic acid, perchloric acid and the like; and examples of the base include sodium hydroxide, potassium hydroxide, lithium hydroxide, barium hydroxide, sodium ethoxide, potassium tert-butoxide, potassium carbonate, sodium carbonate, sodium bicarbonate, aqueous ammonia, pyridine, potassium cyanide, sodium cyanide and the like.

The acid or base is used in an amount of 0.1 equivalent or more, preferably 1 to 50 equivalents, based on Compound (D) or Compound (E), or can also be used as the solvent. The reaction is usually carried out at a temperature between −20° C. and 240° C., preferably between 20° C. and 160° C., if necessary in a sealed tube, and completed in 5 minutes to 140 hours.

Production Method 2

Compound (I) can be obtained by deprotecting the protecting group at the 3-position of Compound (F) or (G) which can be prepared from estrone or a 3-position-protected estrone (for example, acetate, benzoate, methanesulfonate, p-toluenesulfonate, trifluoromethanesulfonate or the like thereof) according to known methods (for example, *Tetrahedron Letters,* 26: 1109 (1985); *Tetrahedron Letters,* 33: 3939 (1992); *Steroids,* 63: 425 (1998); and *Journal of Medicinal Chemistry,* 33: 937 (1990)) or according to the above-described Production Method 1.

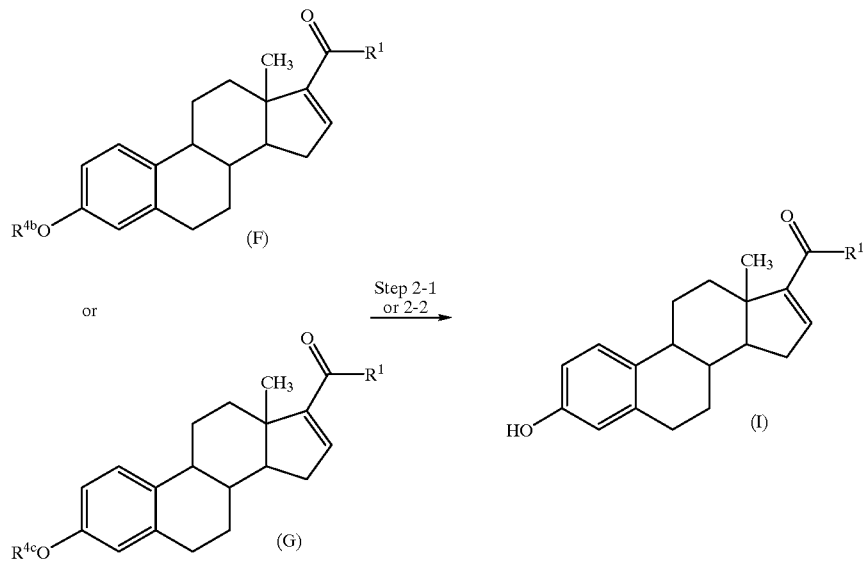

(In the above formula, $R^1$ has the same meaning as defined above; $R^{4b}$ represents alkyl (the alkyl has the same meaning as the alkyl in the above-described alkoxy) or benzyl; and $R^{4c}$ represents acetyl, benzoyl, methanesulfonyl, p-toluenesulfonyl, or trifluoromethanesulfonyl.)

Step 2-1

Compound (I) can be obtained by treating Compound (F) with various deprotecting agents.

Examples of the solvent include dichloromethane, chloroform, 1,2-dichloroethane, DMSO, DMF, quinoline, N-methylpyrrolidine, acetonitrile and the like, which may be used alone or as a mixture thereof.

Examples of the deprotecting agent include boron tribromide, iodotrimethylsilane, sodium sulfide, sodium ethanethiolate, potassium thiophenoxide, hydrobromic acid/acetic acid, aluminum bromide/ethanethiol and the like.

The deprotecting agent is used in an amount of 0.1 equivalent or more, preferably 1 to 20 equivalents, based on Compound (F). The reaction is usually carried out at a temperature between −78° C. and 180° C., preferably between −20° C. and 120° C., and completed in 10 minutes to 48 hours.

Step 2-2

Compound (I) can also be obtained by allowing Compound (G) to react with an acid or a base.

Examples of the solvent include THF, 1,4-dioxane, 1,2-dimethoxyethane, methanol, ethanol, tert-butanol, ethylene glycol, water, acetone, acetonitrile, DMF, DMSO, DMI, toluene, dichloromethane, chloroform, 1,2-dichloroethane and the like, which may be used alone or as a mixture thereof.

Examples of the acid include hydrochloric acid, hydrobromic acid, sulfuric acid, phosphoric acid, trifluoromethanesulfonic acid, trifluoroacetic acid and the like; and examples of the base include potassium carbonate, sodium carbonate, sodium bicarbonate, cesium carbonate, sodium hydroxide, potassium hydroxide, lithium hydroxide, barium hydroxide, sodium ethoxide, potassium tert-butoxide, potassium cyanide, sodium cyanide, aqueous ammonia, diethylamine, butylamine, pyrrolidine, piperidine and the like.

The acid or base is used in an amount of 0.1 equivalent or more, preferably 1 to 20 equivalents, based on Compound (G), or can also be used as the solvent. The reaction is usually carried out at a temperature between −20° C. and 180° C., preferably between 0° C. and 120° C., if necessary in a sealed tube, and completed in 5 minutes to 48 hours.

Production Method 3

Compound (Ic) can be obtained by hydrolyzing an ester or amide group of Compound (Ib), which is Compound (I) in which $R^1$ is alkoxy or $NR^2R^3$ (wherein $R^2$ and $R^3$ have the same meanings as defined above).

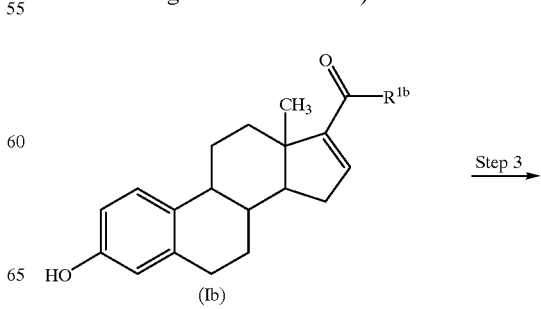

-continued

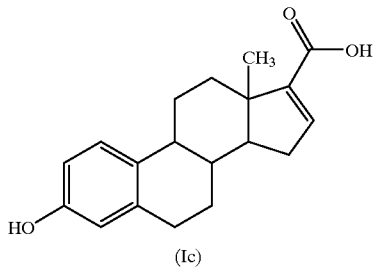

(Ic)

(In the above formula, $R^{1b}$ is alkoxy or $NR^2R^3$ (wherein $R^2$ and $R^3$ have the same meanings as defined above).)

Step 3

Compound (Ic) can be obtained by allowing Compound (Ib) to react with an acid or a base.

Examples of the solvent include THF, 1,4-dioxane, 1,2-dimethoxyethane, methanol, ethanol, tert-butanol, ethylene glycol, water, acetone, acetonitrile, DMF, DMSO, DMI, toluene, dichloromethane, chloroform, 1,2-dichloroethane and the like, which may be used alone or as a mixture thereof.

Examples of the acid include hydrochloric acid, hydrobromic acid, sulfuric acid, phosphoric acid, trifluoromethanesulfonic acid, trifluoroacetic acid, boron tribromide and the like; and examples of the base include potassium carbonate, sodium carbonate, sodium bicarbonate, cesium carbonate, sodium hydroxide, potassium hydroxide, lithium hydroxide, barium hydroxide, sodium ethoxide, potassium tert-butoxide, potassium cyanide, sodium cyanide and the like.

The acid or base is used in an amount of 0.1 equivalent or more, preferably 1 to 20 equivalents, based on Compound (Ib), or can also be used as the solvent. The reaction is usually carried out at a temperature between −78° C. and 180° C., preferably between −20° C. and 120° C., if necessary in a sealed tube, and completed in 5 minutes to 48 hours.

Production Method 4

Compound (Ib) can also be obtained by esterification or amidation of the carboxyl group of Compound (Ic).

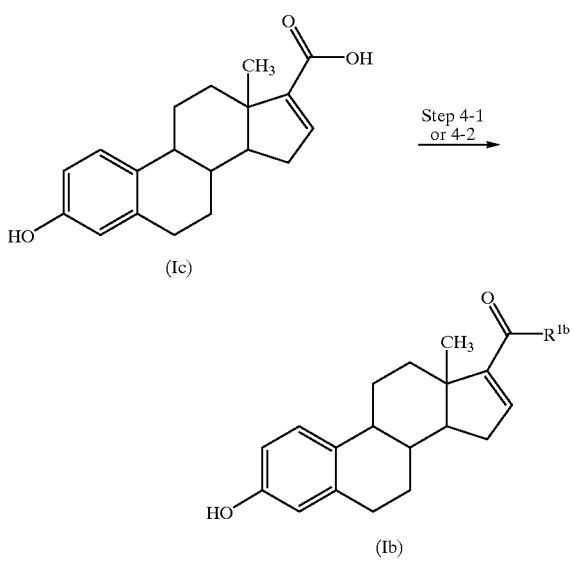

(In the above formula, $R^{1b}$ has the same meaning as defined above.)

Step 4-1

Compound (Ib) can be obtained by allowing Compound (Ic) to react with Compound (II) represented by $HNR^2R^3$ (wherein $R^2$ and $R^3$ have the same meanings as defined above) or an acid addition salt thereof or with Compound (III) represented by $HOR^5$ (wherein $R^5$ has the same meaning as the alkyl in the above-described alkoxy), in the presence of a condensing agent.

Examples of the solvent include THF, 1,4-dioxane, ether, toluene, dichloromethane, chloroform, 1,2-dichloroethane, DMF, acetonitrile and the like, which may be used alone or as a mixture thereof.

Examples of the condensing agent include 1-(3-dimethylaminopropyl)-3-ethylcarbodiimide hydrochloride, N,N'-dicyclohexylcarbodiimide, 1,1'-carbonyldiimidazole, 2-ethoxy-1-ethoxycarbonyl-1,2-dihydroquinoline, triphenylphosphine/carbon tetrachloride and the like, and the reaction can be accelerated by adding an additive agent, such as N-hydroxysuccinimide, 4-(dimethylamino)pyridine, 1-hydroxybenzotriazole hydrate or the like, in an amount of 0.1 to 10 equivalents based on Compound (Ic).

Examples of the acid addition salt of Compound (II) include hydrochloride, hydrobromide, sulfate, nitrate, formate, acetate, oxalate, benzoate, methanesulfonate, p-toluenesulfonate, fumarate, maleate, tartrate and the like.

When an acid addition salt of Compound (II) is used, the reaction can also be carried out in the presence of one equivalent or more, preferably 1 to 20 equivalents, of a base, such as pyridine, triethylamine, diisopropylethylamine, or N,N-diethylaminopyridine, based on the acid addition salt of compound (II). Among these, triethylamine is preferred.

Each of Compound (II) or an acid addition salt thereof, or Compound (III) and the condensing agent is used in an amount of one equivalent or more, preferably 1 to 5 equivalents, based on Compound (Ic). The reaction is usually carried out at a temperature between −20° C. and 80° C., preferably between 0° C. and 40° C., and completed in 5 minutes to 48 hours.

Step 4-2

Compound (Ib) can also be obtained by allowing an acid halide prepared by reacting Compound (Ic) with a halogenating agent to react with Compound (II) represented by $HNR^2R^3$ (wherein $R^2$ and $R^3$ have the same meanings as defined above) or an acid addition salt thereof or with Compound (III) represented by $HOR^5$ (wherein $R^5$ has the same meaning as defined above), in the presence or absence of a base.

Examples of the solvent include THF, 1,4-dioxane, ether, acetone, toluene, dichloromethane, chloroform, 1,2-dichloroethane, water, methanol, acetonitrile, DMF and the like, which may be used alone or as a mixture thereof, and these solvents may not be used in the reaction step with a halogenating agent.

Examples of the halogenating agent include thionyl chloride, thionyl bromide, oxalyl chloride, phosphorus trichloride, phosphorus pentachloride, dichlorotriphenylphosphorane, triphenylphosphine/carbon tetrachloride and the like. The halogenating agent is used in an amount of one equivalent or more, preferably 1 to 20 equivalents, based on Compound (Ic), or may also be used as the solvent.

Examples of the base include potassium carbonate, sodium carbonate, sodium bicarbonate, sodium hydroxide, potassium hydroxide, lithium hydroxide, barium hydroxide, pyridine, triethylamine, diisopropylethylamine, N,N-diethylaminopyridine and the like, and the base is used in an amount of one equivalent or more, preferably 1 to 20 equivalents, based on Compound (Ic) and may also be used as the solvent.

As the acid addition salt of Compound (II), the above-described acid addition salt of Compound (II) can be used.

Compound (II) or an acid addition salt thereof or Compound (III) is used in an amount of one equivalent or more, preferably 1 to 50 equivalents, based on Compound (Ic). The reaction is usually carried out at a temperature between −20° C. and 180° C., preferably between −20° C. and 100° C., and completed in 30 minutes to 48 hours.

In Production Method 4, Compound (Ic) wherein a 3-hydroxy group is protected by an appropriate protecting group such as acetyl, benzoyl, methanesulfonyl, p-toluenesulfonyl, or trifluoromethanesulfonyl (Compound (Ic1)) may be used as the starting material. After a 17-carboxyl group of Compound (Ic1) is converted to the desired group, the desired Compound (Ib) can be obtained by a deprotection method according to Step 2-2. In this case, deprotection at 3-position and conversion of 17-carboxyl group to the desired group can be done simultaneously, by using Compound (II) represented by $HNR^2R^3$ (wherein $R^2$ and $R^3$ have the same meanings as defined above) or a base used in Production Method 4.

Among Compounds (I) of the present invention, compounds in which $R^1$ is hydroxy (Compound (Ic)) or alkoxy (Compound (Id)) are also useful as the starting compounds of compounds (Compound (Aa)) which are Compound (A) described in WO 99/03876 in which $X^p$ and $Y^p$ are combined to represent a double bond. For example, Compound (Aa) can be synthesized from Compound (Ic) or (Id) according to the method described in Production Method 5 or a modified method thereof.

Production Method 5

Compound (Aa) can be obtained by amidation of the carboxyl group of Compound (Ic). It can also be synthesized by carrying out ester-amide exchange reaction of the alkoxycarbonyl group of Compound (Id) which is Compound (I) in which $R^1$ is alkoxy.

(wherein $R^{2p}$ has the same meaning as defined above) or an acid addition salt thereof in the presence of a condensing agent.

Examples of the solvent include THF, 1,4-dioxane, ether, toluene, dichloromethane, chloroform, 1,2-dichloroethane, DMF, acetonitrile and the like, which may be used alone or as a mixture thereof.

Examples of the condensing agent include 1-(3-dimethylaminopropyl)-3-ethylcarbodiimide hydrochloride, N,N'-dicyclohexylcarbodiimide, 1,1'-carbonyldiimidazole, 2-ethoxy-1-ethoxycarbonyl-1,2-dihydroquinoline, triphenylphosphine/carbon tetrachloride and the like, and the reaction can be accelerated by adding an additive agent, such as N-hydroxysuccinimide, 4-(dimethylamino)pyridine, or 1-hydroxybenzotriazole hydrate, in an amount of 0.1 to 10 equivalents based on Compound (Ic).

Examples of the acid addition salt of Compound (IV) include hydrochloride, hydrobromide, sulfate, nitrate, formate, acetate, oxalate, benzoate, methanesulfonate, p-toluenesulfonate, fumarate, maleate, tartrate and the like.

When an acid addition salt of Compound (IV) is used, the reaction can also be carried out in the presence of one equivalent or more, preferably 1 to 20 equivalents, of a base, such as pyridine, triethylamine, diisopropylethylamine, or N,N-diethylaminopyridine, based on the acid addition salt of Compound (IV). Among these, triethylamine is preferred. Each of Compound (IV) or an acid addition salt thereof and the condensing agent is used in an amount of one equivalent or more, preferably 1 to 5 equivalents, based on Compound (Ic). The reaction is carried out at a temperature between −20° C. and 80° C., preferably between 0° C. and 40° C., and completed in 5 minutes to 48 hours.

Step 5-2

Compound (Aa) can also be obtained by allowing an acid halide prepared by reacting Compound (Ic) with a halogenating agent to react with Compound (IV) represented by

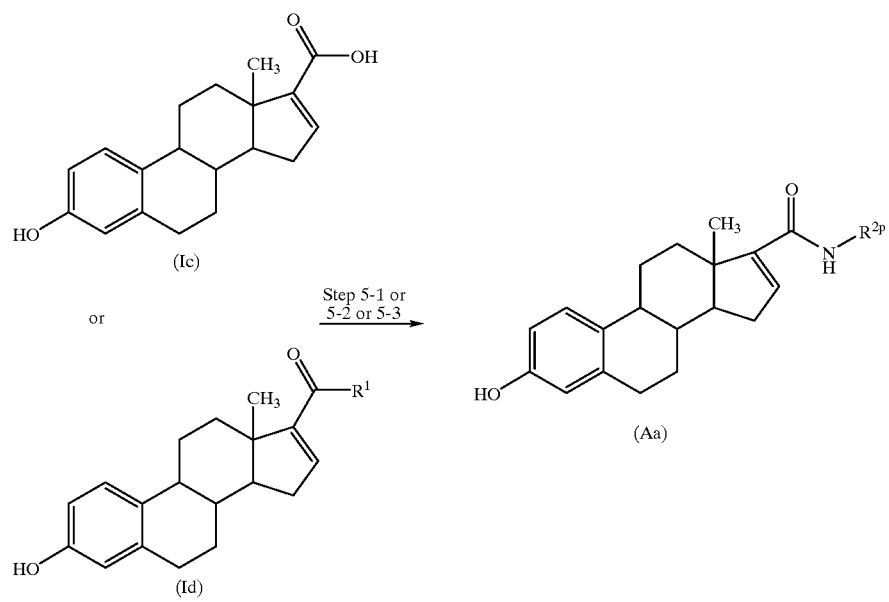

(In the above formula, $R^{1d}$ is alkoxy; and $R^{2p}$ has the same meaning as defined above.)

Step 5-1

Compound (Aa) can be obtained by allowing Compound (Ic) to react with Compound (IV) represented by $H_2NR^{2p}$ $H_2NR^{2p}$ (wherein $R^{2p}$ has the same meaning as defined above) or an acid addition salt thereof in the presence or absence of a base.

Examples of the solvent include THF, 1,4-dioxane, ether, acetone, toluene, dichloromethane, chloroform, 1,2- dichloroethane, water, methanol, acetonitrile, DMF and the like, which may be used alone or as a mixture thereof, and these solvents may not be used in the reaction step with a halogenating agent.

Examples of the halogenating agent include thionyl chloride, thionyl bromide, oxalyl chloride, phosphorus trichloride, phosphorus pentachloride, dichlorotriphenylphosphorane, triphenylphosphine/carbon tetrachloride and the like. The halogenating agent is used in an amount of one equivalent or more, preferably 1 to 20 equivalents, based on Compound (Ic), or may also be used as the solvent.

Examples of the base include potassium carbonate, sodium carbonate, sodium bicarbonate, sodium hydroxide, potassium hydroxide, lithium hydroxide, barium hydroxide, pyridine, triethylamine, diisopropylethylamine, N,N-diethylaminopyridine and the like, which may be used in an amount of one equivalent or more, preferably 1 to 20 equivalents, based on Compound (Ic) or may also be used as the solvent.

As the acid addition salt of Compound (IV), the above-described acid addition salt of Compound (IV) can be used.

Compound (IV) or an acid addition salt thereof is used in an amount of one equivalent or more, preferably 1 to 50 equivalents, based on Compound (Ic). The reaction is usually carried out at a temperature between −20° C. and 180° C., preferably between −20° C. and 100° C., and completed in 30 minutes to 48 hours.

Step 5-3

Compound (Aa) can be obtained by allowing Compound (Id) to react with Compound (IV) represented by $H_2NR^{2p}$ (wherein $R^{2p}$ has the same meaning as defined above) or an acid addition salt thereof.

Examples of the solvent include THF, 1,4-dioxane, ether, toluene, dichloromethane, chloroform, 1,2-dichloroethane, DMF, acetonitrile, methanol, tert-butanol, water, DMSO and the like, which may be used alone or as a mixture thereof. Compound (IV) may also be used as the solvent.

As the acid addition salt of Compound (IV), the above-described acid addition salt of Compound (IV) can be used.

When an acid addition salt of Compound (IV) is used, the reaction can also be carried out in the presence of one equivalent or more, preferably 1 to 20 equivalents, of a base, such as potassium carbonate, sodium carbonate, sodium bicarbonate, sodium hydroxide, potassium hydroxide, lithium hydroxide, barium hydroxide, pyridine, triethylamine, diisopropylethylamine, or N,N-diethylaminopyridine, based on Compound (Id).

The reaction can be accelerated by adding an additive agent, such as sodium cyanide, n-butyl lithium, sodium hydride, sodium methoxide, or trimethylaluminum, in an amount of 0.01 to 2 equivalents based on Compound (Id).

Compound (IV) or an acid addition salt thereof is used in an amount of one equivalent or more, preferably 1 to 10 equivalents, based on Compound (Id). The reaction is usually carried out at a temperature between 0° C. and 180° C., preferably between 30° C. and 180° C., if necessary in a sealed tube or under a pressure of, for example, $2 \times 10^5$ to $1 \times 10^9$ Pascal, preferably $1 \times 10^8$ to $1 \times 10^9$ Pascal, and completed in 30 minutes to 96 hours.

The phenolic hydroxyl group of Compound (Aa) can be substituted with sulfamoyloxy (sulfamoylation) according to the method described in WO 99/03876, the method described in Production Method 6 or a modified method thereof. Also, it is possible to change the order of the above-described reactions, namely the carboxyl group can be converted into amide, or the alkoxycarbonyl group can be converted into amide, after sulfamoylation of the phenolic hydroxyl group.

Additionally, the phenolic hydroxyl group of Compound (I) described by the present application can be sulfamoylated according to the method described in WO 99/03876, the method described in Production Method 6 or a modified method thereof (Compound (V) is a compound which is Compound (I) of the present invention in which the hydroxyl group at the 3-position is sulfamoylated). In this case, it is also possible to change the order of the above-described reactions, namely the carboxyl group can be converted into amide or ester, or the alkoxycarbonyl group can be converted into amide or other ester, after sulfamoylation of the phenolic hydroxyl group.

Production Method 6

Compound (V) can be obtained by sulfamoylation of the 3-position hydroxyl group of Compound (I).

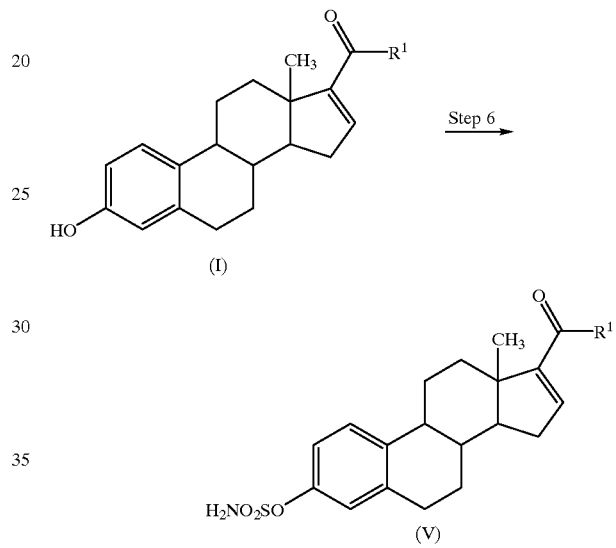

(In the above formula, $R^1$ has the same meaning as defined above.)

Step 6

Compound (V) can be obtained by allowing Compound (I) to react with sulfamoyl chloride or the like in the presence of a base.

Examples of the solvent include THF, 1,4-dioxane, 1,2-dimethoxyethane, ether, DMF, DMSO, DMI, toluene, dichloromethane, chloroform, 1,2-dichloroethane, 1-methyl-2-piperidone and the like, which may be used alone or as a mixture thereof.

Examples of the base include sodium hydride, potassium carbonate, sodium carbonate, sodium bicarbonate, cesium carbonate, potassium tert-butoxide, 2,6-di-tert-butyl-4-methylpyridine, pyridine, 2,6-di-tert-butylpyridine, 2,6-lutidine, triethylamine, diisopropylethylamine, 4-(dimethylamino)pyridine and the like. Among these, sodium hydride and 2,6-di-tert-butyl-4-methylpyridine are preferred.

The base and sulfamoyl chloride are used in an amount of 0.1 equivalent or more, preferably 1 to 20 equivalents, based on Compound (I), or when the base is liquid, it can also be used as the solvent. The reaction is usually carried out at a temperature between −20° C. and 120° C., preferably between 0° C. and 60° C., and completed in 5 minutes to 72 hours.

Additionally to the above-described steps in producing Compound (I), conversion of the functional group of $R^1$ can also be carried out by known methods (for example, *Comprehensive Organic Transformations*, edited by R. C. Larock (1989)).

The compounds prepared by the above-described production methods can be isolated and purified by optional combination of techniques generally used in the organic synthesis, such as filtration, extraction, washing, drying, concentration, crystallization, and various chromatography. The intermediates may be used in succeeding reactions without purification.

In the case where a salt of Compound (I) is desired, when Compound (I) is produced in the form of the desired salt, it can be subjected to purification as such, and when Compound (I) is obtained in its free form, it may be dissolved or suspended in an appropriate solvent and then mixed with a corresponding base to form the salt.

Additionally, Compound (I) or pharmaceutically acceptable salts thereof may exist in the form of addition products with water or various solvents, and these addition products are also included in the scope of the present invention.

Examples of Compound (I) are shown in Table 1. In the following table, Me, Et, $^n$Pr and $^t$Bu mean methyl, ethyl, propyl and tert-butyl, respectively.

TABLE 1

Examples of Compound (I)

| Compound | R$^1$ |
|---|---|
| 1 | OH |
| 2 | OMe |
| 3 | NH$^n$Pr |
| 4 | NH$^t$Bu |
| 5 | NEt$_2$ |

Next, pharmacological activities of typical examples of Compound (I) are described with reference to Test Examples.

TEST EXAMPLE 1

Estrone Sulfatase (Steroid Sulfatase) Inhibition Test:

[6,7-$^3$H] Estrone sulfate (final concentration, 3.3 nmol/L; 300,000 dpm/tube), recombinant human estrone sulfatase (33 ng/tube) and an estra-1,3,5(10),16-tetraene derivative (final concentration, 1 μmol/L) were added to a phosphate buffer (pH 7; final volume, 0.15 mL) containing 0.25 mol/L of sucrose and 0.04 mol/L of nicotinamide, and allowed to enzymatically react for 1 hour at 37° C. The recombinant human estrone sulfatase was obtained by transforming a human estrone sulfatase gene into CHO (Chinese hamster ovary) cells and expressing it in the cells, and used after partial purification. After completion of the enzyme reaction, the reaction solution was mixed with toluene (0.5 mL), followed by stirring, and the mixture was centrifuged for 5 minutes at 9,000 rpm. Thereafter, the toluene extraction layer was separated and the radioactivity of the resulting [$^3$H]-estrone was measured with a liquid scintillation counter. The measurement was carried out by duplication, and the fluctuation within the assay was 10% or less. An enzyme reaction in the absence of the test compound was carried out at the same time. The activity of the test compound to inhibit estrone sulfatase was calculated by the following formula.

Inhibitory activity against estrone sulfatase (%)=100−(100×(A/B))

A: Amount of [$^3$H]-estrone formed in the presence of test compound

B: Amount of [$^3$H]-estrone formed in the absence of test compound

The results are shown in Table 2.

TABLE 2

| Inhibitory activity against estrone sulfatase | |
|---|---|
| Compound | Inhibition % (1 μM) |
| 1 | 48 |

As apparent from the result shown in Table 2, the test compound shows inhibitory activity against steroid sulfatase, so that Compound (I) is useful as an agent for the treatment or prevention of hormone dependent diseases.

Compound (I) or a pharmaceutically acceptable salt thereof can be administered orally or parenterally as it is or in the form of various pharmaceutical compositions. Examples of the dosage form of such pharmaceutical compositions include tablets, pills, powders, granules, capsules, suppositories, injections, drip infusions and the like.

These dosage forms can be prepared by the generally known methods and may contain various additives, such as excipients, lubricants, binders, disintegrating agents, suspending agents, isotonizing agents, emulsifying agents, absorption accelerating agents and the like.

Examples of the carrier in these pharmaceutical compositions include water, distilled water for injection, physiological saline, glucose, fructose, sucrose, mannitol, lactose, starch, corn starch, cellulose, methyl cellulose, carboxymethylcellulose, hydroxypropylcellulose, alginic acid, talc, sodium citrate, calcium carbonate, calcium hydrogenphosphate, magnesium stearate, urea, silicone resin, sorbitan fatty acid ester, glycerin fatty acid ester and the like. These carriers are optionally selected depending on the pharmaceutical preparations.

The dose and frequency of administration of Compound (I) to be used for the above-described purpose may vary depending on various conditions, such as the intended therapeutic or preventive effect, administration method, treating period, age, and body weight, but it may be used by oral administration or parenteral administration (for example, injection, drip infusion, rectal administration by suppositories, skin adhesion and the like) generally in the range of 0.01 to 20 mg/kg per day per adult, and the daily dose may be divided into one to several doses per day.

The present invention provides novel estra-1,3,5(10), 16-tetraene derivatives or pharmaceutically acceptable salts thereof which show inhibitory activity against steroid sulfatase and are useful in treating or preventing hormone dependent diseases.

Examples of the present invention are shown below. $^1$H-NMR used in the examples was measured at 270 MHz, and the measured multiplicity, coupling constant (unit, Hz) and the number of protons are shown in that order in the parentheses just after the δ value of each signal.

EXAMPLE 1

Compound 1

Step 1-1

17-Cyano-3-hydroxyestra-1,3,5(10),16-tetraene 3-methanesulfonate (Compound H) (1.00 g) obtained according to the method described in *The Journal of Organic Chemistry*, 59: 6683 (1994) was dissolved in ethylene glycol (20 mL), and sodium hydroxide (3.36 g) was added thereto, followed by stirring for 10.3 hours under reflux. After completion of the reaction, 6 mol/L hydrochloric acid (13.7 mL) was added to the reaction solution at 0° C. The resulting precipitate was collected by filtration, and washed with water, followed by drying under reduced pressure. The residue was purified by silica gel column chromatography (chloroform/methanol=15/1) to give Compound 1 (3-hydroxyestra-1,3,5(10), 16-tetraene-17-carboxylic acid) (508 mg).

EIMS m/z: 298 (M)$^+$ $^1$H-NMR (DMSO-d$_6$) δ (ppm): 0.87 (s, 3H), 1.25–1.66 (m, 5H), 1.83 (m, 1H), 1.97–2.37 (m, 5H), 2.64–2.87 (m, 2H), 6.44 (d, J=2.3 Hz, 1H), 6.51 (dd, J=2.3, 8.3 Hz, 1H), 6.68 (d, J=3.0 Hz, 1H), 7.03 (d, J=8.3 Hz, 1H), 8.99 (s, 1H) 12.05 (s, 1H)

The structure of Compound H is shown below.

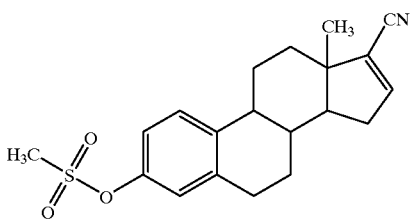

(H)

Step 1-2

Compound 1 can also be obtained by hydrolyzing the ester of Compound 2 obtained in Step 2-2 of the following Example 2.

Compound 2 (methyl 3-hydroxyestra-1,3,5 (10), 16-tetraene-17-carboxylate) (1.21 g) was dissolved in a mixture solvent of methanol (30 mL) and water (10 mL), and lithium hydroxide monohydrate (3.26 g) was added thereto, followed by stirring at room temperature for 19 hours. After completion of the reaction, 1 mol/L hydrochloric acid and chloroform were added to the reaction solution. The resulting precipitate was collected by filtration, and washed with water, followed by drying under reduced pressure to give Compound 1 (3-hydroxyestra-1,3,5(10),16-tetraene-17-carboxylic acid) (0.48 g).

Compound 1 can also be obtained by the following Step 1-3 to Step 1-5.

Step 1-3

Estrone acetate (23.0 g) was dissolved in dichloromethane (70 mL), and 2,6-di-tert-butyl-4-methylpyridine (16.6 g) and trifluoromethanesulfonic anhydride (12.7 mL) were added thereto, followed by stirring at room temperature for 11 hours. An aqueous saturated sodium hydrogen carbonate solution (200 mL) and water (500 mL) were added to the reaction solution, and the reaction mixture was extracted with chloroform. The organic layer was washed with an aqueous saturated sodium hydrogen carbonate solution and then a saturated brine, followed by drying over anhydrous sodium sulfate, and the solvent was evaporated under reduced pressure. The resulting residue was purified by silica gel column chromatography (hexane, and then hexane/ethyl acetate=20/1) to give 17-{((trifluoromethyl)sulfonyl)oxy}estra-1,3,5(10), 16-tetraen-3-yl acetate (28.2 g).

$^1$H-NMR (CDCl$_3$) δ (ppm): 1.00 (s, 3H), 1.36–1.70 (m, 5H), 1.75–1.98 (m, 3H), 2.05–2.20 (m, 1H), 2.28 (s, 3H), 2.26–2.42 (m, 2H), 2.84–2.96 (m, 2H), 5.62 (dd, J=1.3, 3.0 Hz, 1H), 6.80 (d, J=2.3 Hz, 1H), 6.85 (dd, J=2.3, 8.2 Hz, 1H), 7.25 (d, J=8.2 Hz, 1H)

Step 1-4

17-{((Trifluoromethyl)sulfonyl)oxy}estra-1,3,5(10), 16-tetraen-3-yl acetate (23.0 g), triphenylphosphine (989 mg), and triethylamine (35.0 mL) were dissolved in DMF (100 ml), and formic acid (7.13 mL) was added thereto under ice-cooling. Then, palladium (II) acetate (423 mg) was added thereto at room temperature, followed by stirring in a carbon monoxide atmosphere while keeping the temperature for 1 hour. To the reaction solution, 1 mol/L hydrochloric acid (50 mL) and water (1.0 L) were added, and the resulting precipitate was collected by filtration, and dissolved in chloroform (200 mL). The organic layer was dried over anhydrous sodium sulfate, and the solvent was evaporated under reduced pressure. The resulting residue was recrystallized from a mixture solvent of chloroform (300 mL) and hexane (900 mL) to give Compound K (3-acetoxyestra-1,3,5(10),16-tetraene-17-carboxylic acid) (15.3 g).

LC-TOF m/z: 341 [M+H]$^+$; $^1$H-NMR (CDCl$_3$) δ (ppm): 0.96 (s, 3H), 1.35–1.80 (m, 5H), 1.86–2.22 (m, 2H), 2.24–2.50 (m, 4H), 2.28 (s, 3H), 2.80–2.98 (m, 2H), 6.80 (br s, 1H), 6.84 (br d, J=8.6 Hz, 1H), 6.97 (br s, 1H), 7.28 (d, J=8.6 Hz, 1H)

Step 1-5

Compound K (3-acetoxyestra-1,3,5(10), 16-tetraene-17-carboxylic acid) (2.01 g) was suspended in methanol (40 mL), and potassium carbonate (1.66 g) was added thereto, followed by stirring at room temperature for 2 hours. To the reaction solution, 1 mol/L hydrochloric acid (30 mL) and water (100 mL) were added, and the resulting precipitate was collected by filtration and washed with water (100 mL), followed by drying under reduced pressure to give Compound 1 (3-hydroxyestra-1,3,5(10),16-tetraene-17-carboxylic acid) (1.70 g).

The structure of Compound K is shown below.

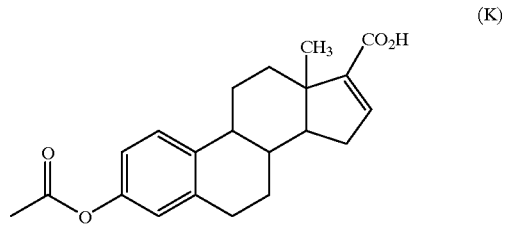

(K)

EXAMPLE 2

Compound 2

Step 2-1

3-Methoxyestra-1,3,5(10),16-tetraene-17-carboxylic acid (Compound J) (2.00 g) obtained according to the method described in *Tetrahedron Letters*, 26: 1109 (1985) was dissolved in dichloromethane (75 mL), and oxalyl chloride (2.3 mL) was added thereto under ice-cooling, followed by stirring at room temperature for 4 hours. After completion of the reaction, the reaction solution was concentrated, the residue was dissolved in dichloromethane (60 mL), and methanol (30 mL) and triethylamine (3.58 mL) were added thereto, followed by stirring at room temperature for 11.5 hours. After completion of the reaction, the reaction solution was concentrated, methanol (20 mL) and 2 mol/L hydrochloric acid (40 mL) were added to the residue, and the resulting precipitate was collected by filtration, and washed with 1 mol/L hydrochloric acid and then water, followed by drying under reduced pressure to give methyl 3-methoxyestra-1,3,5(10), 16-tetraene-17-carboxylate (2.01 g).

Step 2-2

Methyl 3-methoxyestra-1,3,5(10),16-tetraene-17-carboxylate (1.90 g) was dissolved in dichloromethane (30 mL), and boron tribromide (a 1 mol/L solution in dichloromethane) (11.6 ml) was added thereto at −15° C., followed by stirring while raising the temperature up to room temperature over 2 hours. After completion of the reaction, methanol (40 mL) was added to the reaction solution at 0° C., followed by stirring at room temperature for 2 hours. After completion of the reaction, water was added thereto, the reaction mixture was extracted with chloroform, the resulting organic layer was washed with a saturated brine, followed by drying over anhydrous sodium sulfate, and then the solvent was evaporated under reduced pressure. The residue was triturated with a mixture solvent of ethyl acetate and acetone to give Compound 2 (methyl 3-hydroxyestra-1,3,5(10), 16-tetraene-17-carboxylate) (1.58 g).

EIMS m/z: 312 (M)$^+$ $^1$H-NMR (DMSO-d$_6$) δ (ppm): 0.88 (s, 3H), 1.26–1.68 (m, 5H), 1.83 (m, 1H), 2.01–2.40 (m, 5H), 2.65–2.88 (m, 2H), 3.66 (s, 3H), 6.44 (d, J=2.3 Hz, 1H), 6.51 (dd, J=2.3, 8.6 Hz, 1H), 6.77 (s, 1H), 7.03 (d, J=8.6 Hz, 1H), 8.99 (s, 1H)

The structure of Compound J is shown below.

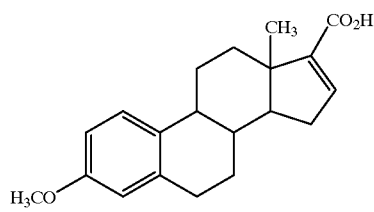

(J)

EXAMPLE 3

Compound 3

Step 3-1

Compound 1 (3-hydroxyestra-1,3,5(10),16-tetraene-17-carboxylic acid) (100 mg) was dissolved in DMF (1.5 mL), 1-(3-dimethylaminopropyl)-3-ethylcarbodiimide hydrochloride (96 mg) and 1-hydroxybenzotriazole hydrate (5 mg) were added thereto under ice-cooling, followed by stirring for 10 minutes, and propylamine (0.041 mL) was added thereto, followed by stirring at the same temperature for 30 minutes, and subsequently stirring at room temperature for 2 hours. After completion of the reaction, water was added to the reaction solution, the reaction solution was extracted with ethyl acetate, the resulting organic layer was washed with a saturated brine, followed by drying over anhydrous sodium sulfate, and the solvent was evaporated under reduced pressure. Ethanol and water were added to the residue, and the resulting precipitate was collected by filtration, and washed with water, followed by drying under reduced pressure. Thereafter, the residue was purified by preparative thin layer chromatography (hexane/ethyl acetate=1/1) to give Compound 3 (3-hydroxy-N-propylestra-1,3,5(10),16-tetraene-17-carboxamide) (70 mg).

FAB-MS m/z: 340 (M+1)$^+$ $^1$H-NMR (CDCl$_3$) δ (ppm): 0.95 (t, J=7.3 Hz, 3H), 1.02 (s, 3H) 1.57 (m, 2H), 1.37–1.73 (m, 5H), 1.86–2.15 (m, 2H), 2.20–2.39 (m, 4H), 2.76–2.97 (m, 2H), 3.29 (dt, J=6.4, 7.3 Hz, 2H), 4.80 (s, 1H), 5.66 (br t, J=6.4 Hz, 1H), 6.32 (dd, J=1.7, 3.3 Hz, 1H), 6.58 (d, J=2.6 Hz, 1H), 6.63 (dd, J=2.6, 8.6 Hz, 1H), 7.14 (d, J=8.6 Hz, 1H)

Compound 3 can also be obtained by the following Step 3-2.

Step 3-2

Compound K (3-acetoxyestra-1,3,5(10),16-tetraene-17-carboxylic acid (14.2 g) was suspended in dichloromethane (100 mL), and oxalyl chloride (14.2 mL) was added thereto under ice-cooling, followed by stirring while keeping the temperature for 10 minutes and then stirring at room temperature for 2 hours. The reaction solution was concentrated under reduced pressure, and the resulting residue was suspended in THF (100 mL), and propylamine (27.5 ml) was added thereto under ice-cooling, followed by stirring at room temperature for 11 hours. Water (400 mL) was added to the reaction solution, and then 6 mol/L hydrochloric acid (60 mL) was added thereto, followed by stirring while keeping the temperature for 30 minutes. The resulting precipitate was collected by filtration, and then recrystallized from acetonitrile (320 mL) to give Compound 3 (3-hydroxy-N-propylestra-1,3,5(10),16-tetraene-17-carboxamide) (12.5 g).

EXAMPLE 4

Compound 4

According to Step 2-1 of Example 2, N-tert-butyl-3-methoxyestra-1,3,5(10),16-tetraene-17-carboxamide was obtained from 3-methoxyestra-1,3,5(10),16-tetraene-17-carboxylic acid (Compound J) and tert-butylamine, and according to Step 2-2 of Example 2, Compound 4 (N-tert-butyl-3-hydroxyestra-1,3,5(10),16-tetraene-17-carboxamide) was obtained from N-tert-butyl-3-methoxyestra-1,3,5(10), 16-tetraene-17-carboxamide.

EIMS m/z: 353 (M)$^+$ $^1$H-NMR (DMSO-d$_6$) δ (ppm): 0.91 (s, 3H), 1.12–1.61 (m, 5H), 1.29 (s, 9H), 1.83 (m, 1H), 1.91–2.36 (m, 5H), 2.64–2.88 (m, 2H), 6.27 (s, 1H), 6.44 (s, 1H), 6.51 (br d, 1H), 6.99 (m, 2H), 8.97 (s, 1H)

EXAMPLE 5

Compound 5

According to Step 2-1 of Example 2, N,N-diethyl-3-methoxyestra-1,3,5(10),16-tetraene-17-carboxamide was obtained from 3-methoxyestra-1,3,5(10),16-tetraene-17-carboxylic acid (Compound J) and diethylamine, and according to Step 2-2 of Example 2, Compound 5 (N,N-diethyl-3-hydroxyestra-1,3,5(10),16-tetraene-17-carboxamide) was obtained from N,N-diethyl-3-methoxyestra-1,3,5(10), 16-tetraene-17-carboxamide.

EIMS m/z: 353 (M)$^+$

While the invention has been described in detail and with reference to specific examples thereof, it will be apparent to one skilled in the art that various changes and modifications can be made therein without departing from the spirit and scope thereof.

What is claimed is:

1. An estra-1,3,5(10),16-tetraene derivative represented by formula (I):

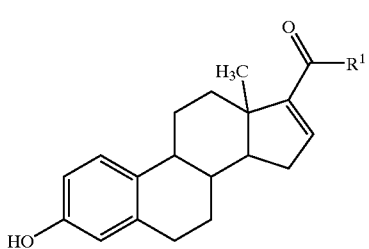

(I)

wherein $R^1$ represents alkoxy (the alkyl moiety of said alkoxy is straight-chain alkyl having 1, 2, or 4–14 carbon atoms or branched-chain alkyl having 1 to 14 carbon atoms), or $NR^2R^3$ (wherein $R^2$ and $R^3$ are the same or different, and each represents hydrogen, straight-chain lower alkyl having 1 to 3 carbon atoms, or branched-chain lower alkyl having 3 to 8 carbon atoms, with the proviso that when one of $R^2$ and $R^3$ is hydrogen, the other is not $CH_2CH_2CH_3$, $CH_2CH(CH_3)_2$, or $C(CH_3)_3$), or a pharmaceutically acceptable salt thereof.

2. The estra-1,3,5(10),16-tetraene derivative according to claim 1, wherein $R^1$ is $NR^2R^3$, or a pharmaceutically acceptable salt thereof.

3. The estra-1,3,5(10),16-tetraene derivative according to claim 1, wherein $R^1$ is alkoxy, or a pharmaceutically acceptable salt thereof.

4. The estra-1,3,5(10),16-teroraene derivative according to claim 2, wherein $R^2$ and $R^3$ independently represent straight-chain lower alkyl having 1 to 3 carbon atom, or branched-chain lower alkyl having 3 to 8 carbon atoms, or a pharmaceutically acceptable salt thereof.

5. The estra-1,3,5(10),16-tetraene derivative according to claim 2, wherein $R^2$ represents hydrogen, and $R^3$ represents straight-chain lower alkyl having 1 to 3 carbon atoms, or branched-chain lower alkyl having 3 to 8 carbon atoms, or a pharmaceutically acceptable salt thereof.

6. A composition for treatment of breast cancer by inhibiting steroid sulfatase, which comprises the estra-1,3,5(10),16-tetraene derivative according to claim 1 or a pharmaceutically acceptable salt thereof, and a pharmaceutically acceptable carrier.

7. A method for inhibiting steroid sulfatase in a person requiring such treatment, which comprises administering a therapeutically effective amount of an estra-1,3,5(10),16-tetraene derivative represented by formula (I):

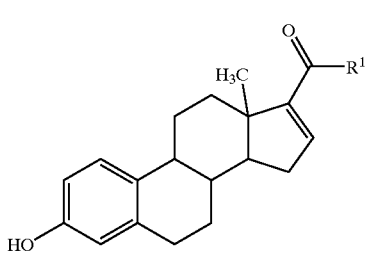

(I)

wherein $R^1$ represents alkoxy (the alkyl moiety of said alkoxy is straight-chain alkyl having 1, 2, or 4–14 carbon atoms or branched-chain alkyl having 1 to 14 carbon atoms), or $NR^2R^3$ (wherein $R^2$ and $R^3$ are the same or different, and each represents hydrogen, straight-chain lower alkyl having 1 to 3 carbon atoms, or branched-chain lower alkyl having 3 to 8 carbon atoms, with the proviso that when one of $R^2$ and $R^3$ is hydrogen, the other is not $CH_2CH_2CH_3$, $CH_2CH(CH_3)_2$, or $C(CH_3)_3$), or a pharmaceutically acceptable salt thereof.

8. The method according to claim 7, wherein $R^1$ is $NR^2R^3$.

9. The method according to claim 7, wherein $R^1$ is alkoxy.

10. The method according to claim 8, wherein $R^2$ and $R^3$ independently represent straight-chain lower alkyl having 1 to 3 carbon atom, or branched-chain lower alkyl having 3 to 8 carbon atoms, or a pharmaceutically acceptable salt thereof.

11. The method according to claim 8, wherein $R^2$ represents hydrogen, and $R^3$ represents straight-chain lower alkyl having 1 to 3 carbon atoms, or branched-chain lower alkyl having 3 to 8 carbon atoms, or a pharmaceutically acceptable salt thereof.

12. A method for treating a person having breast cancer associated with the overproduction of estrone produced from estrone sulfate, which comprises administering a therapeutically effective amount of an estra-1,3,5(10),16-tetraene derivative represented by formula (I):

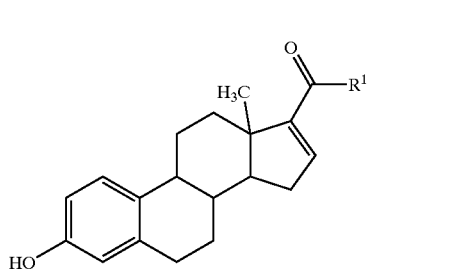

(I)

wherein $R^1$ represents alkoxy (the alkyl moiety of said alkoxy is straight-chain alkyl having 1, 2, or 4–14 carbon atoms or branched-chain alkyl having 1 to 14 carbon atoms), or $NR^2R^3$ (wherein $R^2$ and $R^3$ are the same or different, and each represents hydrogen, straight-chain lower alkyl having 1 to 3 carbon atoms, or branched-chain lower alkyl having 3 to 8 carbon atoms, with the proviso that when one of $R^2$ and $R^3$ is hydrogen, the other is not $CH_2CH_2CH_3$, $CH_2CH(CH_3)_2$, or $C(CH_3)_3$), or a pharmaceutically acceptable salt thereof.

13. The method according to claim 12, wherein $R^1$ is $NR^2R^3$.

14. The method according to claim 12, wherein $R^1$ is alkoxy.

15. The method according to claim 13, wherein $R^2$ and $R^3$ independently represent straight-chain lower alkyl having 1 to 3 carbon atom, or branched-chain lower alkyl having 3 to 8 carbon atoms, or a pharmaceutically acceptable salt thereof.

16. The method according to claim 13, wherein $R^2$ represents hydrogen, and $R^3$ represents straight-chain lower alkyl having 1 to 3 carbon atoms, or branched-chain lower alkyl having 3 to 8 carbon atoms, or a pharmaceutically acceptable salt thereof.

* * * * *